United States Patent [19]

Gipson

[11] 4,215,059

[45] Jul. 29, 1980

[54] BORIDE CATALYST FOR EPOXIDIZING OLEFINIC COMPOUNDS

[75] Inventor: Robert M. Gipson, Austin, Tex.

[73] Assignee: Texaco Development Corporation, White Plains, N.Y.

[21] Appl. No.: 699,837

[22] Filed: Jun. 25, 1976

Related U.S. Application Data

[62] Division of Ser. No. 565,004, Apr. 4, 1975, Pat. No. 4,038,290.

[51] Int. Cl.² ............................................. C07D 301/20
[52] U.S. Cl. ................................................. 260/348.29
[58] Field of Search .................... 260/348.5 L, 348.29

[56] References Cited

U.S. PATENT DOCUMENTS

| | | | |
|---|---|---|---|
| 3,413,134 | 11/1968 | Kaufman et al. | 423/297 |
| 3,489,775 | 1/1970 | Seree de Roch et al. | 260/348.5 L |
| 3,634,464 | 1/1972 | Wulff et al. | 260/348.5 L |
| 3,666,412 | 5/1972 | Sowards | 252/432 |
| 3,702,855 | 11/1972 | Bell et al. | 260/348.5 L |
| 3,832,363 | 8/1974 | Fetterly et al. | 260/348.5 V |

*Primary Examiner*—Norma S. Milestone

*Attorney, Agent, or Firm*—James L. Bailey; Walter D. Hunter

[57] ABSTRACT

A novel catalyst material of a boron containing substance for catalyzing the liquid phase oxidation of an olefin with an organic hydroperoxide to the corresponding oxirane is disclosed. The novel catalyst materials are characterized as binary or ternary boride compounds having the general formula $M_xB_y$ or $M_xB_yR_z$ wherein x is an integer from 1-5; y is an integer from 1-2; z is an integer from 1-4; B is boron; M is an element selected from the groups II-A, III-B, IV-B, V-B, VI-B, VII-B, VIII, III-A, IV-A, and V-A of the Periodic Table, the rare earths, and the actinides; and R is an element different from M selected from the same group of elements in the Periodic Table as M. The preferred catalyst materials are those boron containing substances which are substantially insoluble in the reaction mixture containing the organic hydroperoxides, olefins and products.

Also disclosed is a method for liquid phase epoxidation of an olefinic compound with an organic hydroperoxide at lower temperatures, e.g. 25° C. to 200° C. and a pressure sufficient to maintain the mixture substantially in liquid phase in the presence of a catalytically effective amount of the novel catalyst material.

7 Claims, No Drawings

BORIDE CATALYST FOR EPOXIDIZING OLEFINIC COMPOUNDS

This is a division, of application Ser. No. 565,004, filed Apr. 4, 1975 now U.S. Pat. No. 4,038,290.

BACKGROUND OF THE INVENTION

1. Field of the Invention

This invention pertains to catalyst material for expediting the oxidation of an olefin to the corresponding oxirane; and, more particularly to a catalyst material of a boron containing substance for catalyzing the liquid phase epoxidation of olefins with organic hydroperoxides.

2. Prior Art

Oxiranes or epoxides, while being valuable commercial products in and of themselves, are also commercially valuable as starting reactants for synthesizing many useful compounds such as polyether polyols for urethane systems. Over the years many methods have been disclosed for synthesizing such compounds. The majority of these methods involve the oxidation of the corresponding olefin. For example, it is known that ethylene can be converted to the corresponding epoxide by a vapor phase partial oxidation with molecular oxygen over a silver catalyst. However, the ease of olefin oxidation varies greatly depending upon the size and structure of the olefinic starting reactant and therefore many of the disclosed processes are not effective for epoxiding olefins in general.

Recently it has been disclosed that olefinically unsaturated organic compounds can be oxidized to the corresponding oxirane compound in liquid phase with organic hydroperoxides in the presence of various catalysts. For example, U.S. Pat. No. 3,350,422 issued Oct. 31, 1967 to Kollar discloses that soluble vanadium compounds can be employed as a homogeneous catalyst for oxidation of olefins with organic hydroperoxide. Specifically, hydrocarbon soluble organometallic compounds of vanadium are disclosed as being effective as epoxidation catalysts. However, the insoluble vanadium catalysts, such as for example, vanadium pentoxide are disclosed as substantially ineffective in catalyzing the epoxidation of propylene. More recently, U.S. Pat. No. 3,634,464 issued Jan. 11, 1972 to Wulff, et al. describes the use of oxides of molybdenum on a solid inorganic oxide support modified by inclusion therewith of bismuth or certain rare earth metal oxides as a catalyst for the epoxidation of olefins with an organic hydroperoxide. The catalyst is substantially insoluble in the epoxidation reactant mixture, providing a heterogeneous system. The presence of a minor proportion of bismuth or certain rare earth oxides as catalyst modifiers is disclosed as a critical feature of the catalytic action.

Additionally, it has been disclosed that silicides or siliceous solids having high surface to mass ratio are particularly effective as catalytic substances in the epoxidation of olefins with organic hydroperoxides. Specifically, U.S. Pat. No. 3,702,855 issued Nov. 14, 1972 to Bell et al. discloses a catalytic material selected from metal silicides of titanium, zirconium, vanadium, mobium, chromium, molybdenum, and tungsten is effective as a liquid phase epoxidation catalysts.

More recently it has been disclosed in U.S. Pat. No. 3,832,363 issued Aug. 27, 1974 to Fetterly et al. that the epoxidation of ethylenic compounds to the corresponding oxirane compound is catalyzed by the presence of a boron oxide, a dehydrated boric acid, and the hydrocarbyl esters thereof. The compounds disclosed in this patent which are useful as catalysts contain at least one B-O-B linkage.

The previously described catalysts suffer from one or more disadvantages when employed as liquid phase epoxidation catalysts. For example, many of the previously known catalyst materials are expensive and difficult to prepare, and/or are highly selective to oxidation of specific olefinic compounds, and/or are difficult to use requiring special apparatus or highly selective reaction conditions, and/or are limited to heterogeneous or homogeneous type reaction systems.

Unexpectedly it has been found that a large class of boron containing substances are effective in catalyzing liquid phase epoxidation of an olefin with an organic hydroperoxide to the corresponding oxirane. These substances may be generally categorized as binary and ternary boride compounds consisting of boron and at least one element selected from groups II-A, III-B, IV-B, V-B, VI-B, VII-B, VIII, III-A, IV-A and V-A of the Periodic Table, the rare earths and the actinides. Because of the wide range of boron containing substances effective in catalyzing liquid phase epoxidation of an olefin with an organic hydroperoxide, the catalyst may be selected to form a substantially heterogeneous system with the reactants or a substantially homogeneous system with the reactants. Further, boron containing substances of the instant invention are easily obtainable, relatively inexpensive and easy to handle. Because of the wide range of boron substances which are shown catalytically active, a particular compound can be matched to a particular epoxidation reaction thus achieving somewhat superior selectively and yield. Mixtures of these boron substances can also be used to afford specific selectivity.

SUMMARY OF THE INVENTION

According to the invention, a catalyst material of a boron containing substance useful for the epoxidation of an olefinic unsaturated compound with an organic hydroperoxide consists essentially of substances containing boron and at least one element selected from groups II-A, III-B, IV-B, V-B, VI-B, VII-B, VIII, III-A, IV-A, and V-A of the Periodic Table, the rare earths, and the actinides. Specifically the catalyst material of the instant invention may be characterized as the binary borides and the ternary borides having the general formula respectively $M_xB_y$ and $M_xB_yR_z$ wherein x is an integer from 1 to 5; y is an integer from 1 to 12; z is an integer from 1 to 4; B is boron; M is a single element selected from the above grouping and R is an element selected from the above grouping but different from M.

According to a preferred embodiment, the catalyst material is a boron containing substance generally characterized as a binary boride which is not dissolved or attacked by the reaction mixture containing the organic hydroperoxide, olefins, and by-products.

According to another aspect of the invention, the epoxidation of an olefinically unsaturated compound to a corresponding oxirane derivative employing organic hydroperoxide as an epoxidizing agent is carried out in the presence of a catalytic amount of the boron containing substance at lower temperatures under liquid phase conditions.

DETAILED DESCRIPTION OF THE PREFERRED EMBODIMENT

The catalyst materials in accordance with a preferred embodiment are those boron containing substances which are not substantially dissolved or attacked by the reactants or product mixtures under the reaction conditions encountered in the epoxidation of olefinic compound to the corresponding oxirane with organic hydroperoxides. These catalyst materials may be generally employed in the liquid phase heterogeneous epoxidation systems wherein organic compounds having at least one aliphatic olefinically unsaturated carbon-carbon bond and from 2 to 60 carbon atoms are oxidized with an organic hydroperoxide. Further, a preferred epoxidation is carried out in the presence of certain borides as hereinafter particularly described in the presence of reactants and under conditions as further set forth herein.

Catalyst Materials

The catalysts used within the scope of the instant invention are generally boron containing substances effective in catalyzing the liquid phase epoxidation of an olefin with an organic hydroperoxide. These substances are characterized as boride compounds of boron and at least one element selected from group II-A, III-B, IV-B, V-B, VI-B, VII-B, VIII, III-A, IV-A and V-A of the Periodic Table, the rare earth and the actinides. More particularly these boride compounds may be either the so-called binary borides or the ternary borides. The binary borides may be represented by the general formula $M_xB_y$ wherein B is boron; M is an element selected as above; x is an integer from 1 to 5; B is boron and y is an integer from 1 to 12. The ternary borides may be represented by the general formula $M_xB_yR_z$ wherein M, x, B and y represent elements or integers as described herein above, R is an element selected from the same periodic groupings as M but is an element different from M in any given compound and z is an integer from 1 to 5.

The preferred catalytic materials are the binary borides. The preferred binary boride compounds are those catalysts which are not dissolved or attacked by the reaction mixtures containing the organic hydroperoxides, olefins, and products. The preferred catalytic materials thus form substantially heterogeneous systems with the liquid reactants and products. Preferred catalysts are $LaB_6$, $CeB_6$, $ZrB_2$, $NbB$, $WB$, $W_2B_5$, $MnB$, $NiB$, $AlB_2$, and $AlB_{12}$. Other examples of boride compounds useful as insoluble catalysts are $CaB_6$, $TiB_2$, $ZrB_{12}$, $HfB_2$, $TaB_2$, $FeB$, $Co_3B$, $Co_2B$, $CoB$, $SiB_4$, $SiB_6$, and $B_4C$.

It should be noted that the empirical formulas given herein do not necessarily represent the exact stoichiometry of the catalytic material but rather represent particular crystalline phases which may be nonstoichiometric due to lattice defects, vacant sites and the like. It is intended that the scope of the instant invention cover all of the so-called binary and ternary borides represented by the formulas set out herein above, which include but are not limited to borides having isolated boron atoms such as for example $M_4B$, $M_3B$, $M_2B$, $M_5B_2$ and $M_7B_3$; borides having single and double chains of boron atoms, i.e. those crystalline structures where a boron, boron linkage exist such as $M_3B_2$ and $M_4B_3$ and $M_3B_4$; borides having two dimensional nets such as those represented by the formula $MB_2$ and $M_2B_5$; and borides having a three dimensional boron network such as those having the formulas $MB_4$, $MB_6$, and $MB_{12}$.

As used herein, solubility and insolubility are relative terms. That is, those boron containing compounds which are characterized as forming heterogeneous systems may be in fact somewhat soluble in the reaction mixtures. Likewise, so-called soluble boron containing substances may not form a completely homogeneous single phase with the reactants and reaction products. When utilizing the so-called soluble boron containing substances, it is preferable that sufficient catalyst be used to create a heterogeneous system.

The exact physical form of the catalyst is not important. It may be used as a powder, lumps, pellets, spheres, and the like; as adherent films on metals or other supports; and as coatings on supports such as alumina, silica or clay. Additionally, the catalyst of the instant invention may be extruded or compressed to various shapes as to form a combination with adhering materials such as binders, fillers, extenders, and the like.

Additionally, it will be realized by those skilled in the art that mixtures of one or more of the boride catalytic material may be used to provide, for example, selectivity in epoxidizing certain olefinic compounds.

Olefinically Unsaturated Reactants

The olefinically unsaturated materials which can be epoxidized in accordance with the invention are generally organic-compounds having at least one aliphatic olefinically unsaturated carbon-carbon double bond containing from 2 to about 60 carbon atoms. In fact there are no known olefinically unsaturated organic compounds which cannot be utilized within the scope of the instant invention. For example, the olefinic reactant may be of acyclic, monocyclic, bicyclic, or polycyclic olefin and may be a monoolefin, or a polyolefin. Additionally, the olefinic linkages of the polyolefins may be conjugated or nonconjugated. Further, the olefinic reactant may be a hydrocarbon or a substituted hydrocarbon with functional groups containing, for example, oxygen, halogen, nitrogen, or sulfur. Typical substituted functional groups are hydroxy groups; ether groups; ester groups; halogens such as chlorine and florine; nitrile groups; amide groups; sulfur containing groups; nitrate groups; and the like. Examples of suitable olefinic reactants include ethylene, propylene, isobutylene, hexene-2, octene-1, eicosene-1, pipyrlene, vinylcyclohexene, dicyclopentadiene, styrene, allyl chloride, allyl alcohol, allyl acetate, allyl ether, allyl cyanide, cyclohexenecarbonitrile, soy bean oil, cotton seed oil and the like.

Organic Hydroperoxides

The organic hydroperoxides which can be used within the scope of the instant invention are broadly any organic compound having at least one hydroperoxide moiety but free of functional groups which are deleterious to the epoxidation reaction or are normally reactive with the hydroperoxides. A group of useful hydroperoxides is represented by the formula R'—OOH wherein R' is a hydrocarbyl or a substituted hydrocarbyl group containing from 3 to 20 carbon atoms. The hydrocarbyl group may be alkylaryl, alkyl or substituted alkyl or arylalkyl. The substituted alkyl or arylalkyl hydrocarbyl can contain oxygen incorporated into the functional group such as hydroxy, hydrocarbyloxy, hydrocarbyloxycarbonyl, hydrocarboyloxy, and the like. Additionally, the hydrocarbyl or substituted hydrocarbyl can contain halogens, e.g., chlorine, florine, bromine and iodine.

The most preferred hydroperoxides are secondary and tertiary hydroperoxides containing up to about 15 carbon atoms such as tertiary butyl hydroperoxide, tertiary amyl hydroperoxide, cyclohexene hydroperoxide, tetralin hydroperoxide, cumene hydropeoxide, diisopropyl benzenehydroperoxide, α-methyl benzylhydroperoxide, and the like.

Reaction Conditions

The epoxidation process of the instant invention is conducted in the liquid phase at lower temperatures, e.g. 25° C. to 200° C. and pressures sufficient to maintain the reactants and products substantially in solution. The mode of conducting the process of this invention is not critical and may be accomplished by conventional methods such as batch, continuous or semi-continuous reactions. The temperature range at which the epoxidation reaction is carried out will depend upon the reactant and the catalyst employed but generally temperatures in the range from about 25° C. to 200° C. and preferably temperatures of about 50° C. to about 150° C. are found sufficient. The reaction pressures are generally those which are required to maintain the reactants, products, and the like substantially in liquid phase. Pressures which range from autogenous to about 200 atmospheres are generally sufficient for carrying out the instant process.

The amount of reactants present in the reaction mixtures will generally depend upon the olefin to be epoxidized and the hydroperoxide; but, generally molar ratios of olefin to hydroperoxide of from about b 1:10 to 100:1 and preferably from 1:2 to 10:1 have been found sufficient. Additionally, the molar ratios of hydroperoxide to the catalyst material will likewise depend upon the boron containing substance used, the olefin, the hydroperoxide and the reaction condition. Generally molar ratios of hydroperoxide to catalyst from about 1:1 to 10,000:1 have been found sufficient, and preferably molar ratios of 1:1 to 1,000:1 are utilized.

Although it is not necessary, diluents and/or solvents which are liquid at reaction temperatures and pressures and are substantially nondeleterious under reaction conditions to the reactant and products may be utilized. Useful solvents and diluents include aliphatic or aromatic hydrocarbons, alcohols, ethers, and esters. Aliphatic and aromatic halogenated hydrocarbons may also be utilized. Examples of suitable solvents include tertiary butyl alcohol, octane, cyclohexane, benzene, toluene, ethyl benzene, dichloromethane, ethylene dichloride, propylene dichloride, chlorobenzene, and the like.

Additionally, additives such as antioxidants and inorganic bases may be added to the reaction mixture if desired. Examples of such additives are di-t-butyl-p-cresol, p-methoxyphenol, diphenylamine, sodium oxide, magnesium oxide, and the like. Additives of these types are particularly useful for preventing undesirable side reactions.

The epoxidation reaction is suitably conducted by any of a variety of procedures. In accordance with one procedure the olefinic reactant and the catalyst are initially charged into a suitable vessel equipped for reflux at autogenous pressure. The vessel is heated to reaction temperatures and hydroperoxide is then added incrementally with constant stirring. In another method, the reaction is effected in a continuous manner such as by contacting the olefin reactant and the organic hydroperoxide, in the presence of a solid catalyst which may be supported on a medium. In accordance with another method, the catalyst and the hydroperoxide in a suitable solvent may be charged into an autoclave which is sealed and flushed with nitrogen. The olefinic compound is then pressured into the sealed autoclave and the reaction mixture heated to reaction temperatures and stirred while reaction pressures are maintained. This method is particularly suited to gaseous olefinic compounds such as ethylene and propylene.

At the conclusion of the reaction, the product mixture can be separated and the product recovered by conventional methods such as fractional distillation, selective extraction, filtration, and the like. Further, the catalyst, unreacted reactants, solvents and diluents if such are used can be recycled.

To further illustrate the process and the catalyst of the instant invention the following examples are provided not as limitation but by further way of demonstrating the details of the invention.

EXAMPLE 1

In this example, the liquid phase epoxidation of an olefinic compound with an organic hydroperoxide was carried out in the presence of a catalytic amount of a boron containing substance in accordance with the instant invention. A 250 ml. flask equipped with a stirrer, thermometer, reflux condenser and dropping funnel was charged with 84 g. octene-1 and 1 g. tungsten boride (WB). The charged mixture was heated to 90° C. and 90% tertiary butyl hydroperoxide was added dropwise until a total of 25 g. has been added. The reaction mixture was then heated at reflux (108°–110° C.) for 220 minutes with stirring. The heated mixture was allowed to cool and then the crude reaction product was analyzed. The analysis indicated a 36% yield of octene oxide based on the amount of charged hydroperoxide. The crude reaction product was filtered by conventional methods and the resulting filtrate was analyzed for metal content by atomic absorption analysis. No metals were detected in the filtrate.

EXAMPLE 2–30

In these examples, various boron containing substances were used to catalyze the liquid phase epoxidation of octene-1 with tertiary butyl hydroperoxide by the procedure of Example 1. The results are shown in Table I.

TABLE 1

| Example | Catalyst (wt. g) | Moles octene | Moles hydroperoxide | Time, Hours | Conversion hydroperoxide | Selectvity (based on hydroperoxide) to epoxide | Selectivity (based on converted octene) $S_2$ |
|---|---|---|---|---|---|---|---|
| 2 | LaB$_6$(1) | 0.375 | 0.125 | 6.0 | 82% | 20% | 88% |
| 3 | CeB$_6$(1) | 0.375 | 0.125 | 5.0 | 90% | 87% | 94% |
| 4 | TiB$_2$(1) | 0.75 | 0.25 | 7.0 | 16% | 18% | 40% |

TABLE 1-continued

| Example | Catalyst (wt. g) | Moles octene | Moles hydro- peroxide | Time, Hours | Conversion hydro- peroxide | Selectvity (based on hydro- peroxide) to epoxide | Selectivity (based on converted octene) $S_2$ |
|---|---|---|---|---|---|---|---|
| 5 | $ZrB_2(3)$ | 0.75 | 0.125 | 6.0 | 89% | 87% | 92% |
| 6 | NbB(3) | 0.75 | 0.125 | 7.0 | 89% | 91% | 91% |
| 7 | TaB(1) | 0.375 | 0.125 | 6.0 | 73% | 15% | 90% |
| 8 | $TaB_2(1)$ | 0.375 | 0.125 | 6.0 | 62% | 16% | 78% |
| 9 | WB(2) | 0.75 | 0.125 | 7.0 | 86% | 92% | 92% |
| 10 | MnB(3) | 0.75 | 0.125 | 6.0 | 52% | 27% | 84% |
| 11 | $Co_3B$-$Co_2B(1)$ | 0.375 | 0.125 | 3.0 | 96% | 15% | 88% |
| 12 | CoB(1) | 0.375 | 0.125 | 5.0 | 92% | 29% | 90% |
| 13 | NiB(1) | 0.375 | 0.125 | 6.0 | 68% | 81% | 93% |
| 14 | FeB(2) | 0.375 | 0.125 | 6.0 | 45% | 22% | 86% |
| 15 | $AlB_2(3)$ | 0.75 | 0.125 | 6.0 | 66% | 88% | 89% |
| 16 | $AlB_{12}(1)$ | 0.375 | 0.125 | 5.0 | 95% | >90% | 94% |
| 17 | $B_{12}C_3(1)$ | 0.375 | 0.125 | 6.0 | 47% | 10% | 74% |
| 18 | $SiB_4(1)$ | 0.75 | 0.125 | 5.0 | 76% | 42% | 83% |
| 19 | $SiB_6(1)$ | 0.375 | 0.125 | 6.0 | 66% | 18% | 92% |
| 20 | BN(1) | 0.375 | 0.125 | 6.0 | 47% | 10% | 89% |
| 21 | $CaB_6(1)$ | 0.275 | 0.125 | 6.0 | 65% | 23% | 86% |
| 22 | $W_2B_5(2)$ | 0.375 | 0.125 | 6.0 | 75% | 81% | 94% |
| 23 | $VB_2(1)$ | 0.375 | 0.125 | 3.0 | 99% | 49% | 93% |
| 24 | CrB(2) | 1.25 | 0.25 | 4.0 | 80% | 14% | 55% |
| 25 | $CrB_2(1)$ | 0.375 | 0.125 | 5.0 | 82% | 21% | 73% |
| 26 | $Cr_5B_3(1)$ | 0.375 | 0.125 | 6.0 | 86% | 19% | 69% |
| 27 | MoB(1) | 1.50 | 0.50 | 1.75 | 95% | 82% | 87% |
| 28 | $MoB_2(1)$ | 0.75 | 0.25 | 2.0 | 98% | 71% | 98% |
| 29 | $ZrB_{12}(2)$ | 0.375 | 0.125 | 6.0 | 81% | 53% | 90% |
| 30 | $UB_2(2)$ | 0.375 | 0.125 | 6.0 | 95% | 11% | 67% |

EXAMPLE 31

In this example, propylene oxide was prepared in accordance with the instant invention. A stirred one liter autoclave was charged with 2 g. of tungsten boride (WB), 50 g. tertiary butyl hydroperoxide, and 100 g. tertiary butanol. The autoclave was sealed and flushed with nitrogen. Then 84 g. of propylene were pressured into the sealed autoclave and the reaction mixture was heated with stirring at 118° to 122° C. for 4 hours. The pressure maintained in the autoclave during the reaction sequence was substantially autogenous. Propylene oxide yield values using GLC A% analysis were >65%.

EXAMPLE 32

In this example, the procedure in Example 31 was repeated with the exception that the solvent used was 100 g. benzene instead of the tertiary butanol. Propylene oxide yield values using GLC A% were >90%.

EXAMPLE 33

In this example, the procedure in Example 31 was repeated with the exception that the solvent was 100 g. propylene dichloride instead of the tertiary butanol. Propylene oxide yield values using GLC-A% were >90%.

EXAMPLE 34

In this example octene oxide was prepared by a method similar to that of Example 1 with the exception that 25 g. of cumene hydroperoxide was used as the epoxidizing agent instead of tertiary butyl hydroperoxide. A significant yield of octene oxide was observed.

EXAMPLE 35

In this example, N-octene oxide was prepared by the method of Example 34 with the exception that aluminum dodecaboride ($AlB_{12}$) was utilized as a catalyst instead of tungsten boride. A significant yield of octene oxide was observed.

EXAMPLES 36–39

In each of the following examples branched chain and cyclic olefinic compounds were epoxidized in accordance with the invention, using the procedures as set out in Example 1. The following epoxides were prepared from the corresponding olefin by reaction with tertiary butyl hydroperoxide in the presence of a catalytic amount of tungsten boride (WB). The results are shown in Table II.

TABLE II

| Olefin (g) | Catalyst Tungsten Boride g | Hydro- peroxide Tertiary Butyl g | Conver- sion Hydro- peroxide | Selec- tivity epoxide (based on hydro- peroxide) |
|---|---|---|---|---|
| 36 Vinylcyclohexene (42) | 4 | 10 | 91% | 93%[1] |
| 37 Allyl Acetate (32) | 4 | 10 | 10% | 80%[2] |
| 38 3-Cyclohexene Carbonitrile (17) | 4 | 8 | 52% | 90%[2] |
| 39 Dicyclopentadiene (60) | 4 | 10 | 92% | 39%[2] |

[1] Analysis based uupon GLC area %
[2] Analysis based upon titration-wt %

EXAMPLE 40

In this example epichlorohydrin was produced in accordance with the instant invention. A glass pressure bottle fitted with a stirrer was charged with 100 g. allylchloride, 25 g. 90% t-butylhydroperoxide and 3 g. tungsten boride (WB). The charged mass was heated to 108° C.-110° C. with stirring and held for 24 hours. The pressures maintained during the reaction sequence was autogeneous. Recoverable amounts of epichlorohydrin were observed.

EXAMPLE 41

In this example ethylene oxide was produced in accordance with the instant invention. A stirred one liter autoclave was charged with 12 g. aluminum dodecaboride ($AlB_{12}$) 50 g. tertiary butyl hydroperoxide and 150 g. tertiary butyl alcohol. The autoclave was sealed and flushed with ethylene and pressurized. The autoclave was heated to 110° C. and a pressure of 800 psig maintained for 4 hours. During this period, the temperature range of the reaction mixture varied from about 109° C.-112° C. The effluent reaction product mixture showed recoverable amounts of ethylene oxide.

While the invention has been explained in relation to its preferred embodiment, it is to be understood that various modifications thereof will become apparent to those skilled in the art upon reading the specification and is intended to cover such modifications as fall within the scope of the appended claims.

What is claimed is:

1. A method for the liquid phase epoxidation of an olefin having from about 2 to about 60 carbon atoms with an organic hydroperoxide comprising the step of:
    intimately contacting said olefin with said organic hydroperoxide at lower temperatures of about 25° C. to about 200° C. and pressures sufficient to maintain the product and reactants substantially in liquid phase in the presence of a catalytically effective amount of a binary boride of boron and a metal selected from the group consisting of tungsten, molybdenum and chromium.

2. The method of claim 1 wherein said nonboron element is tungsten.

3. The method of claim 1 wherein said binary boride compounds are selected from a group consisting of a WB and $W_2B_5$.

4. The method of claim 1 wherein said nonboron element is molybdenum.

5. The method of claim 1 wherein said binary boride is selected from a group consisting of MoB and $MoB_2$.

6. The method of claim 1 wherein said nonboron element is chromium.

7. The method of claim 1 wherein said binary boride is selected from a group consisting of CrB, $CrB_2$ and $Cr_5B_3$.

* * * * *